United States Patent [19]

Bertini et al.

[11] Patent Number: 4,888,283

[45] Date of Patent: Dec. 19, 1989

[54] SELECTIVE INHIBITORS OF BENZYLAMINOXIDASES WITH RESPECT TO OTHER AMINOXIDASES

[75] Inventors: Vincenzo Bertini, Cosenza; Angela De Munno, Pisa; Francesco Lucchesini, Rende; Franca Buffoni, Florence; Barbara Bertocci, Pistoia, all of Italy

[73] Assignee: Consiglio Nazionale Delle Ricerche, Rome, Italy

[21] Appl. No.: 193,236

[22] Filed: May 11, 1988

Related U.S. Application Data

[62] Division of Ser. No. 846,681, Apr. 1, 1986.

[30] Foreign Application Priority Data

Apr. 1, 1985 [IT] Italy ..................... 47906 A/85

[51] Int. Cl.⁴ .............. A61K 31/13; C07C 85/00; C12N 9/99; C07D 213/60
[52] U.S. Cl. ..................... 435/184; 435/189; 564/388; 564/389; 564/390; 564/391
[58] Field of Search ............. 438/184, 189; 564/388, 564/389, 390, 391

[56] References Cited

U.S. PATENT DOCUMENTS

| | | | |
|---|---|---|---|
| 1,989,093 | 1/1935 | Hartung | 564/385 X |
| 2,553,441 | 5/1951 | Chenicel | 564/389 X |
| 3,070,628 | 12/1962 | Lemin | 564/385 X |
| 3,320,314 | 5/1967 | Houlihan | 564/385 X |
| 3,399,226 | 8/1968 | Saari | 564/389 X |
| 3,639,423 | 2/1972 | Winter et al. | 564/385 X |
| 3,951,970 | 4/1976 | Razdan et al. | 564/389 X |
| 3,960,958 | 6/1976 | Richardson | 564/389 |
| 4,014,937 | 3/1977 | Richardson | 564/385 X |
| 4,073,942 | 2/1978 | Keck et al. | 564/385 X |
| 4,388,250 | 6/1983 | Farber et al. | 564/389 X |

OTHER PUBLICATIONS

Chem Abs 99-84197(11), "Biochem Int.", V7(1), 89-94 (1983), Bancelli et al.
Chem Abs 96-49615(7), "J. Pharm. Pharmacol", V33(9), 569-75 (1981), Lewinsohn, Rachel.
Chem Abs 99-20255(3), Biochem J. V211(3), pp. 767-769 (1983), Buffoni et al.
Chemical Abstracts, vol. 103, No. 15, Oct. 14, 1985.
Chemical Abstracts, vol. 60, No. 10, May. 11, 1964.
Chemical Abstracts, vol. 90, No. 17, Apr. 23, 1979.
Chemical Abstracts, vol. 97, No. 3, Jul. 19, 1982.
Annals New York Academy of Sciences, vol. 107, 1963, pp. 811-821.
Reagents for Organic Synthesis, vol. 1, 1967.
Chem Abs 97-16947(3), Biochem Pharmacol, V31(5), pp. 825-830 (1982), Andree et al.
Weygand et al., "Chem. Ber.", vol. 101, No. (10), pp. 3623-3641 (1968).
Fieser et al., "Synthetic Organic Reagents", vol. 1, pp. 55-56 (1967).

Primary Examiner—Herbert J. Lilling
Attorney, Agent, or Firm—Pollock, Vande Sande & Priddy

[57] ABSTRACT

Selective inhibitors of benzylaminoxidases, said inhibitors consisting of compounds of the general formula I

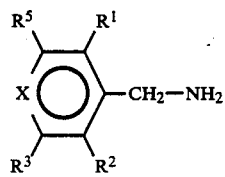

wherein X is a group C—$R^4$ or a nitrogen atom, $R^1$ and $R^2$, which can be the same or different from each other, represent hydrogen, hydroxyl groups, alkoxyl groups, or alkyl, alkenyl, hydroxyalkyl, alkoxyalkyl, hydroxyalkoxyalkyl, hydroxyalkoxyl, alkoxyalkoxyl, hydroxyalkoxyalkoxyl, phenoxyl or phenoxyalkyl groups or their substitution derivatives in the phenoxyl group, provided that no more than one of the same be hydrogen, and one or more of the symbols $R^3$, $R^4$ or $R^5$ are hydrogen atoms or alkyl or hydroxyl or alkoxyl or hydroxyalkyl or hydroxyalkoxyl or hydroxyalkoxyalkyl or haloalkyl or carbonyl or carboxylic or ester or amido or nitrile or sulfonic groups or halogen atoms or nitro groups.

11 Claims, No Drawings

SELECTIVE INHIBITORS OF BENZYLAMINOXIDASES WITH RESPECT TO OTHER AMINOXIDASES

This application is a division of application Ser. No. 846,681, filed Apr. 1, 1986.

The present invention relates to synthetic organic compounds for the selective inhibition of benzylaminoxidases with respect to other aminoxidases.

More particularly, this invention relates to organic compounds suitable for causing the selective inhibition of benzylaminoxidases (BAO) with respect to diaminoxidases (DAO), to lysyloxidases (LAO) and to monoaminoxidases of the A and the B types [MAO (A), MAO (B)].

Benzylaminoxidase belongs to the class of copper-containing aminoxidases (E.C.1.4.3.6). Such class comprises many enzymes which catalyze the oxidative deamination of various monoamines or polyamines through a similar reaction mechanism and which differentiate by the substrate specificity.

In the recent years, the interest for copper-containing aminoxidases has increased remarkably because of the discoveries:

(1) of lysyloxidase (LAO), a copper-depending enzyme which catalyzes the formation of crosslinking of elastic fibres and collagen (S. R. Pinnel and G. R. Martin, Proc. Natl. Acad. Sci. USA 61, 708 (1968));

(2) of the very important role of the intracellular levels of polyamines and of putrescine in the cellular proliferation, which levels are controlled both by the activity of ornithinodecarboxylase and by diaminooxidases (DAO) as well as by sperminoxidases (SAO) (C. V. Porter, Science, 219, 1083 (1983); F. Buffoni, Trends in Pharmacological Sciences, 4, 313 (1983));

(3) of the ubiquitous presence within tissues of an enzyme of said class, which enzyme has been called the "semicarbazide-sensitive aminoxidase" (SSAO), that is found at quite high concentrations in the connective tissue and in the smooth muscles, in particular in the vessel tissues (R. Lewinsohn, J. Pharm. Pharmacol., 33, 369 (1981); F. Buffoni, L. Della Corte and D. B. Hope, Proc. Roy. Soc. Lond. B, 195, 417 (1977)).

The physiological roles of the latter class of enzymes (i.e., SSAO), as well as the role of aminoxidases which are present in the blood of mammalians including man (i.e., benzylaminoxidase (BAO) and sperminoxidase (SAO)), are not well known.

It has been shown that BAO which is present in the blood comes from the connective tissue (F. Buffoni, L. Della Corte and D. B. Hope, Proc. Roy. Soc. Lond. B., 195, 417 (1977) and that said SSAO's show generally a very high affinity for benzylamine, so that they are benzylaminoxidases which are not necessarily the same as the connective tissue BAO's. Indeed, two different BAO's have been found in the swine aorta (F. Buffoni, M. Marino, R. Pirisino, Ital. J. Biochem., 25, 191 (1976)).

Even though the physiological role of said BAO's is unknown, some experimental data show that BAO's levels in the blood change in the case of some pathological conditions, and more particularly, such levels increase in the case of cirrhosis (C. M. McEwen and D. O. Castell, J. Lab. Clin. Med., 70, 36 (1967); F. Buffoni, G. Ignesti, R. Pirisino and C. Cortesini, Medical Biology, 55, 109 (1977)) and in the case of some fibrotic conditions, whereas they decrease in the case of some tumoral forms (R. Lewinsohn, Clin. Chim. Acta, 81, 247 (1977)).

Very recent researches have shown that there is an increase in the BAO's levels during the neovascularization process (G. Banchelli, M. Ziche, P. Dolara, F. Buffoni, Acta Pharmacol. Tox. 53, 40 (1983)).

There are no selective inhibitors of BAO's at the present time, as the inhibitors known up to now are also active on the other aminoxidases of the same class at concentrations of the same order.

The most active inhibitors among those which are known are the carbonyl compounds reagents such as hydroxylamine, hydrazine and hydrazide derivatives, semicarbazide, and alpha-aminoguanidine.

Moreover, BAO's are inhibited by cyanides as well as by the chelating agents of bivalent copper, such as diethyldithiocarbamate and cuprizone. Low-selective and reversible inhibitors are also known, such as cysteamine, papaverine, bulbocapnine, amphetamine, and alphamethylbenzylamine (F. Buffoni and L. Della Corte, Adv. Biochem. Psycopharmacol., 5, 133 (1972)).

High concentrations of beta-aminopropionitrile ($I_{50} > 10^{-2}M$), which is a lathyrogenous active on LAO's, inhibit also said BAO's irreversibly.

Beta-aminopropionitrile (BAPN) is a substrate of BAO's, and cyanoacetaldehyde which is formed is responsible for the irreversible inhibition (Raimondi L., Banchelli G., Bertocci B., Lodovici M., Ignesti G., Pirisino R., Buffoni F., Bertini V. and De Munno A., Agents and Actions, 16, 95 (1985)) through a reaction mechanism that is likely to be similar to the mechanism determined by other suicidal substrates such as 1-phenyl-1-fluoro-2-aminoethane.

Useful practical applications can be obtained in the pharmaceutical field from the selective inhibitors of said BAO's.

Indeed, such compounds can be supposed to slow the fibrotic processes so that such compounds could be employed in quite a large range of therapeutic applications in some pathological conditions as for instance cirrhosis, essential stabilized hypertension, diabetes, arthrosis, etc. (Buffoni F., Trends in Pharmacological Sciences, 4, 313 (1983)). Moreover, their potential activities are of much importance in the neovascularization processes (G. Banchelli, M. Ziche, P. Dolara, F. Buffoni, Biochem. Pharm., in press. Acta Pharmacol. Tox. 53, 40 (1983)).

In order to satisfy the need for selective inhibitors of BAO's some experimental observations were carried out beforehand, which observations pointed out that the oxidation reaction mechanism catalyzed by benzylaminoxidases (BAO's) can be ascribed to the capability shown by copper contained in the enzyme of coordinating around itself at the same time both the amino group of the substrate and an oxygen molecule as well as of favouring the transfer of a hydride ion from the $CH_2$ group of the substrate bearing the amino group to the same oxygen. Such transfer puts to end the oxidation reaction promoted by BAO; indeed, the carbon atom that left said hydride ion can receive two electrons from the nitrogen of the amino group bonded to the same so as to form a protonated imine which after hydrolysis corresponds to aldehyde and ammonia, whereas the oxygen molecule that received a hydride ion forms the $HOO^-$ ion which is typical of deprotonated hydrogen peroxide. The aldehyde, ammonia and hydrogen peroxide are the normal products which can be separated from the oxidation reactions of amines, said reaction being catalized by BAO.

It was also observed experimentally in a preliminary way that the selective inhibition of the BAO enzyme can be traced to situations which, with amines that can be referred to the optimal substrates, prevent, for instance through coordination exchange or through steric hindrance or through the formation of a hydrophobic barrier, molecular oxygen as well as the amino group from coordinating simultaneously around copper, so that the transfer is also hindered of the hydride ion. The enzyme coordinated to the amine which thus fails completely or partially to transfer said hydride ion can thus become blocked.

On that bases, the selective inhibitors of benzylaminoxidases (BAO's) were surprisingly found which are the object of the present invention and consist of the chemical compounds corresponding to the general formula I:

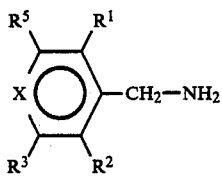

wherein X is a C—$R^4$ group or a nitrogen atom, $R^1$ and $R^2$, which can be the same or different from each other, represent hydrogen, hydroxyl groups, alkoxyl groups, alkyl, alkenyl, hydroxyalkyl, alkoxyalkyl, hydroxyalkoxyalkyl, hydroxyalkoxyl, alkoxyalkoxyl, hydroxyalkoxyalkoxyl, phenoxyl, phenoxyalkyl groups or their substitution derivatives in the phenoxyl group, with the provision that no more than one of the same be hydrogen, and one or more of the symbols $R^3$, $R^4$ or $R^5$ are hydrogen atoms or alkyl groups or hydroxyl, alkoxyl, hydroxyalkyl, hydroxyalkoxyl or hydroxyalkoxyalkyl or haloalkyl or carbonyl or carboxylic or ester or amido or nitrile or sulfonic groups or halogen atoms or nitro groups.

By preference the compounds of the formula I are employed according to the present invention in which the aliphatic hydrocarbon residues which are possibly present as contained in the groups $R^1$, $R^2$, $R^3$, $R^4$ and $R^5$ are made up of hydrocarbon chains containing up to 15 carbon atoms, while the alkoxyl system sequences contain, if they are present, up to seven consecutive alkoxyl systems, and the carbon and oxygen atom chains possibly present and variously intercalated contain up to 14 carbon atoms.

Preferably, the inhibitors corresponding to the general formula I are prepared, stored and employed in the form of salts, such as for instance in the form of their hydrochlorides.

The inhibitors corresponding to the general formula I are prepared by different procedures according to the nature of the groups $R^1$, $R^2$, $R^3$, $R^4$, $R^5$ and X. The examples shown in the following for illustrative purposes and not for limitative purposes put into evidence the reactions as well as the syntheses of the new compounds obtained within the scope of the present invention.

For instance, the inhibitors according to the present invention corresponding to the general formula I, wherein $R^1$ and $R^2$ are alkoxyl groups or their derivatives are prepared advantageously by a procedure comprising the operation of:

(a) synthesising the benzenic systems containing said alkoxyl groups or their derivatives, at the 1,3 positions, (b) introducing lithium into the 2 position of the benzenic system 1,3-bisostituted according to step (a), employing n-butyl-lithium for introduction of Li, (c) transforming the compounds according to step (b) into benzaldehyde derivatives by reaction with dimethylformamide, (d) transforming the aldehydes according to step (c) into oximes, and (e) reducing oximes according to (d) into the final benzylamino-compounds.

It is to be observed that the introduction of lithium, which is favoured by the complexing action of the alkoxyl groups, was much easily performed with all various compounds of such class which were previously unknown, which were employed as reactants.

More particularly, the reduction operation (e) of all various oximes so treated, and previously unknown, if carried out by the Raney alloy, is advantageous with respect to other reduction methods known in the literature.

The enzymic inhibitors which are the object of the present invention are different chemical compounds that, each one of them with its own features, are capable of corresponding to the mechanism criteria of the inhibition process mentioned beforehand and are the basis of the present invention. Such inhibitors are accordingly necessarily numerous and they can be traced to classes of chemical derivatives corresponding to the general formula I.

The inhibitors which are the object of the present invention are chemical compounds, previously unknown but, as they can be traced to classes of derivatives, some of them in some classes can by chance turn out to be already known; however, the inhibiting character towards benzylaminoxidases had not been discovered for any of them, up to now.

As a confirmation of the fact that the selective inhibitors of BAO's can be traced to classes of derivatives, three compounds already known in the literature and which are not described as inhibitors of aminoxidases have been prepared again and their activities have been tested (examples 5, 6 and 7). It has been found that said compounds are active indeed, though at a low degree, as inhibitors of BAO and at a lower extent, of other aminoxidases.

The inhibitors which are the object of the present invention can reach very high inhibition powers towards benzylaminoxidases (BAO's), with $IC_{50}$ (M) values of the order of $10^{-7}$, whereas the same compounds inhibit the aminooxidases DAO, LAO, MAO (A) and MAO (B) just at quite a low degree, showing $IC_{50}$ (M) values which are about $10^4$–$10^5$ times greater than those relevant to BAO.

In order to illustrate the present invention better and to make its employment easier, some illustrative examples are disclosed in the following, but said examples are not to be considered as limitative of the scope of the present invention as shown in the enclosed claims.

The inhibition activity in such examples is estimated by investigating each chemical compound from two viewpoints, i.e., as the substrate and as the inhibitor of various copper-containing aminoxidases (E.C.1.4.3.6) and of the FAD-depending monoaminoxidases (E.C.1.4.3.4):

(a) As the substrate

The oxidation of the compound is estimated in all cases by measuring the production of $H_2O_2$. Such operation is carried out within a temperature-controlled bath set at 37° C. and stirred, in the presence of air. The production of $H_2O_2$ is quantitatively determined by the method of H. P. Lehman, K. H. Schosinsky, M. F. Beeler (Clin. Chem., 20, 1564 (1974)).

(b) As the inhibitor

The inhibition of various enzymes is studied in all cases by previous incubation of the compound with the enzymes for 30 minutes before the addition of the substrate up to saturating concentrations.

The quantitative determination of benzylaminoxidases (BAO's) is carried out by the isotopic procedure disclosed by F. Buffoni and G. Ignesti (Biochem. J.; 145, 369 (1975)) employing $^{14}C$-benzylamine as the substrate at the final concentration of 1,7 mM.

The quantitative determination of the diaminoxidases (DAO's) is performed by the isotopic method disclosed by J. Kusche, H. Richter, R. Hesterberg, J. Schmidt, W. Lorenz, (Agents and Actions, 3, 148-156 (1973)) employing $^{14}C$-putrescine as the substrate at the final concentration of 1 mM.

The quantitative determination of lysyloxidase (LAO) is carried out by the isotopic procedure of J. Melet, G. D. N. E. Vianden, B. N. Bachra (Anal. Biochem., 77, 141 (1977)) employing as the substrate $^{3}H$-elastine prepared as disclosed by S. R. Pinnell, and G. R. Martin (Proc. Natl. Acad. Sci. USA 61, 708 (1968)) and isolated as disclosed by L. B. Sandberg, N. W. Weissman, D. W. Smith (Biochemistry, 8, 2940 (1969)). (The $^{3}H$-elastine employed shows the following properties: concentration of $^{3}H$-lysin 0.135±0.014 nmol/mg; radioactivity 3±0.44 μC/mg (average values±s.e. of 5 preparations); elastine is employed at the final concentration of 0.150 mg/ml, such concentration being found optimal).

The quantitative determination of monoaminoxidases (MAO's) is carried out by the same procedure as the determination of BAO's, but $^{14}C$-beta-phenylethylamine is employed at the final concentration of 1.7 mM.

The enzymes employed

The following oxidases are employed:
Pure BAO obtained from swine plasma by the procedure disclosed by F. Buffoni and H. Blaschko (Proc. Roy. Soc. B 161, 153 (1964)); DAO from swine kidney, as obtained and purified by the Sigma (St. Louis, Md., USA, 0.25 U/mg); purified LAO from swine aorta obtained by the procedure disclosed by F. Buffoni and L. Raimondi (Agents and Actions, 11, 38 (1981)). Rat liver mitochondria obtained by the procedure disclosed by G. W. Schneider and G. H. Hogeboon (J. Biol. Chem., 183, 123 (1950)) were employed as the source of MAO.

The labeled compounds

[DL-6$^{3}H$ (N)]lysine was obtained from the New England Nuclear, Boston, Mass., USA; [7-$^{14}C$]benzylamine was obtained from the ICN Pharmaceutical, Inc., Irvine, Calif., USA; [1,4-$^{14}C$]putrescine, and 2-phenyl-[1-$^{14}C$]ethylamine were obtained from the Radiochemical Centre, Amersham, U.K..

The determination of the $IC_{50}$ (M) values, of the reversibility and of the inhibition type.

$IC_{50}$ (M)=The molar concentration of the inhibitor that inhibits 50% of the enzyme activity at a saturating concentration of the substrate. Said concentration is calculated from curves obtained by pre-incubation of the compound for 30 minutes (at 6 different concentrations) with the enzyme before adding the substrate and determining the enzymic rate.

The repetition of the experiments allows to obtain the average values of the $IC_{50}$ (M) as well as the relative standard errors.

The reversibility of the effect was evaluated showing that the inhibition caused by a certain concentration of the inhibitor (for instance the $IC_{50}$ value) would be reverted by dialysis of the solution.

The inhibition type was evaluated by studying the effect of the compound on the enzymic rate (v) at 5 different concentrations of the substrate (s) and plotting the results by the classical procedure as 1/v vs. 1/s according to Lineweaver-Burk.

The meaning of the symbols used in the examples as regards the activity tests.

n=number of the experiments
$IC_{50}(M)$=molar concentration of inhibitor that inhibits the enzyme activity by 50% at a saturating concentration of the substrate
r=reversible inhibition
i=irreversible inhibition
pr=partially reversible inhibition
c=competitive inhibition
nc=not competitive inhibition
m=mixed inhibition
s=the compound is the substrate
ns=the compound is not the substrate

EXAMPLE 1

Synthesis and activity of an inhibitor of the formula

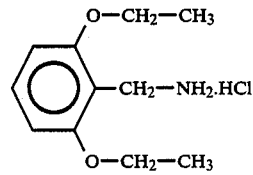

10 g of resorcinol dissolved in 30 ml of anhydrous N,N-dimethylformamide are added over 30 minutes and with stirring to a suspension of 4.99 g of sodium hydride in 60 ml of anhydrous N,N-dimethylformamide, while keeping the temperature at 0° C. After the addition the mixture is stirred for 3 hours at room temperature, then it is cooled to 0° C. and treated with stirring in a period of 10 minutes with 32.75 g of ethyl bromide. The mixture is then kept stirred overnight at room temperature, and next it is diluted with 200 ml of water and extracted with 150 ml of benzene, this volume being divided into three portions. The benzene extracts, after washing with an aqueous solution of sodium hydroxide at the concentration of 10% then with water, and after distillation at atmospheric pressure till elimination of the solvent and next under reduced pressure, give 1,3-diethoxybenzene with yield of 78%; boiling point 105°-107° C.:4 Torr (H. H. Hodgson, H. Clay, J. Chem. Soc., 1872 (1930), boiling point 234°-235° C.).

A solution of 14.20 g of 1,3-diethoxybenzene in 250 ml of anhydrous ether, is added with 64 ml of a 1,6 M solution of n-butyllithium in n-hexane. The mixture is refluxed under nitrogen for 21 hours, then it is cooled with ice and treated with 9.9 ml of anhydrous N,N-dimethylformamide. The mixture is allowed to stand at room temperature overnight and then it is poured into a solution of 30 ml of concentrated hydrochloric acid in 200 ml of water, then stirred and extracted with 200 ml of ethyl ether, which volume is divided into two portions. The ether extracts are dried with anhydrous sodium sulfate and then they are evaporated to dryness. The residue gives after recrystallization from n-hexane the 2,6-diethoxybenzaldehyde with yield of 56%; melting point is 56°-58° C.

A suspension of 9.00 g of 2,6-diethoxybenzaldehyde in 25 ml of water is added with 3.54 g of hydroxylamine hydrochloride and with 3.24 g of sodium hydroxide, then said suspension is stirred at room temperature till the appearance of a large amount of a solid. The mixture is saturated with carbon dioxide and filtered. The solid, after recrystallization from benzene, gives the oxime of the diethoxybenzaldehyde with yield of 92%; melting point is 160°-161° C.

A mixture which is made up of 100 ml of a 2N water solution of sodium hydroxide and 110 ml of 95% ethanol is added with 8.90 g of the oxime of the 2,6-diethoxybenzaldehyde and with 7.89 g of the nickelaluminium Raney alloy while kept magnetically stirred, then said mixture is stirred for 45 minutes. The reaction mixture is filtered and nickel is washed on the filter with about 100 ml of 95% ethanol. The clear filtered solution is adjusted to pH=1 with concentrated hydrochloric acid, then the solvent is removed under reduced pressure and the salt residue is taken with 100 ml of water, then adjusted to pH 12 with a concentrated solution of sodium hydroxide and extracted with 150 ml of n-pentane, this volume being divided into three portions. The pentane extracts, after drying with solid potassium hydroxide, are distilled till the solvent is totally removed, then they are dissolved into 100 ml of anhydrous ethyl ether and saturated with gaseous hydrogen chloride. The salt that is separated, after filtration and drying under vacuum, is recrystallized from acetonitrile so as to obtain the 2,6-diethoxybenzylamine hydrochloride with yield of 88%; melting point is 200°-202° C. I.R. (KBr) 2615 cm$^{-1}$ (NH$_3^{30}$), 1261 cm$^{-1}$ (aromatic C—O), 777 cm$^{-1}$ (phenyl).

Activity of the compound as an inhibitor and as a substrate

BAO: n=4, $IC_{50}(M)$=1.8±0.8×10$^{-7}$, pr, m, ns;

DAO: n=4, $IC_{50}(M)$=1.25±0.01×10$^{-2}$, s;

LAO: $IC_{50}(M)$>1×10$^{-3}$;

MAO: n=4, $IC_{50}(M)$=6.4±0.5×10$^{-3}$, ns.

EXAMPLE 2

Synthesis and activity of the inhibitor of the formula

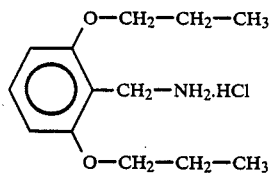

10 g of resorcinol, after reaction with 1-bromopropane in a way similar to that disclosed for the preparation of 1,3-diethoxybenzene (example 1), are transformed into 1,3-di(n-propoxy)benzene with yield of 66%; boiling point 85°-87° C./0.3 Torr (W. C. Wilson, R. Adams, J. Am. Chem. Soc., 45, 528 (1923), boiling point 127°-128° C./12 Torr).

5.38 g of 1,3-di(n-propoxy)benzene are transformed into 2,6-di(n-propoxy)benzaldehyde which is a liquid at room temperature by operating in a way similar to that disclosed for the preparation of 2,6-diethoxybenzaldehyde (example 1), said 2,6-di(n-propoxy)benzaldehyde being purified by crystallization from a mixture of ethyl ether/n-hexane at −78° C.; the yield so obtained is 53%. I.R. (film) 1688 cm$^{-1}$ (C=O), 1597 cm$^{-1}$ (phenyl), 1257 cm$^{-1}$ (aromatic C—O), 782 cm$^{-1}$ (phenyl).

3.26 g of 2,6-di(n-propoxy)benzaldehyde are transformed into the oxime of the 2,6-di(n-propoxy)benzaldehyde by operating in a way similar to that disclosed for the preparation of the oxime of 2,6-diethoxybenzaldehyde (example 1); the yield so obtained is 85%; melting point after crystallization from a mixture of benzene/hexane is 111°-113° C.

2.54 g of the oxime of the 2,6-di(nipropoxy)benzaldehyde are transformed into the 2,6-di(n-propoxy)benzylamine hydrochloride by operating in a way similar to that disclosed for the preparation of the 2,6-diethoxybenzylamine hydrochloride (example 1), said 2,6-di(n-propoxy)benzylamine hydrochloride showing a melting point after crystallization from a mixture of acetonitrile/ethyl ether of 145°-147° C.; yield obtained is 56%. I.R. (KBr) 2600 cm$^{-1}$ (NH$_3^+$), 1257 cm$^{-1}$ (aromatic C—O), 777 cm$^{-1}$ (phenyl).

Activity of the compound as an inhibitor and as a substrate

BAO: n=4, $IC_{50}(M)$=2,4±0.6×10$^{-7}$, pr, m, ns;

DAO: $IC_{50}(M)$>1×10$^{-3}$, s weak;

LAO: $IC_{50}(M)$>1×10$^{-3}$;

MAO: $IC_{50}(M)$>1×10$^{-3}$, s.

EXAMPLE 3

Synthesis and activity of the inhibitor of the formula

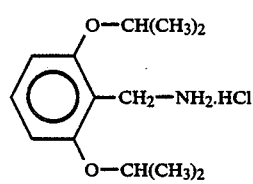

10 g of resorcinol, after reaction with 2-bromopropane in a way similar to that disclosed for the preparation of 1,3-diethoxybenzene (example 1), are transformed into 1,3-diisopropoxybenzene with yield of 44%; boiling point is 103°-104° C./4 Torr (H. H. Hodgson, H. Clay, J. Chem. Soc., 869 (1932), boiling point 237°-238° C.).

3.90 g of 1,3-diisopropoxybenzene are transformed into 2,6-diisopropoxybenzaldehyde, which is a liquid at room temperature, operating in a way similar to that disclosed for the preparation of 2,6-diethoxybenzaldehyde (example 1), said 2,6-diisopropoxybenzaldehyde being purified by flash chromatography eluting the same from Merck silica gel 60 (230-400 mesh) with petroleum ether (boiling point 60°-70° C./ethyl acetate (7/2) as the eluting solvent; yield obtained is 45%. I.R. (film) 1687 cm$^{-1}$ (C=O), 1595 cm$^{-1}$ (phenyl), 1253 cm$^{-1}$ (aromatic C—O), 782 cm$^{-1}$ (phenyl).

1.64 g of 2,6-diisopropoxybenzaldehyde are transformed into the oxime of 2,6-iisopropoxybenzaldehyde operating in a way similar to that disclosed for the preparation of the oxime of 2,6-diethoxybenzaldehyde (example 1), the yield being of 75%; melting point is 153°-155° C. after crystallization from benzene.

1.21 g of the oxime of 2,6-diisopropoxybenzaldehyde are transformed into 2,6-diisopropoxybenzylamine hydrochloride operating in a way similar to that disclosed for the preparation of 2,6-diethoxybenzylamine (example 1), said 2,6-diisopropoxybenzylamine hydrochloride having melting point of 132°-134° C. after crystallization from a benzene/hexane mixture; yield is 53%. I.R. (KBr) 2590 cm$^{-1}$(NH$_3$+), 1261 cm$^{-1}$(aromatic C—O), 780 cm$^{-1}$ (phenyl).

Activity of the compound as a inhibitor and as a substrate

BAO: $IC_{50}(M) > 1 \times 10^{-3}$, s weak;

DAO: $IC_{50}(M) > 1 \times 10^{-3}$, s weak;

LAO: $IC_{50}(M) > 1 \times 10^{-3}$;

MAO: $IC_{50}(M) > 1 \times 10^{-3}$, s weak.

EXAMPLE 4

Synthesis and activity of the inhibitor of the formula:

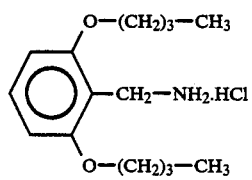

10 g of resorcinol are reacted with 1-bromobutane in a way similar to that disclosed for the preparation of 1,3-diethoxybenzene (example 1), and then transformed into 1,3-di(n-butoxy)benzene with yield of 73%; boiling point is 106°-109° C./0.3 Torr (K. R. Irani et al., J. Univ. Bombay, 18, 1 (1950); C.A., 45, 1974c (1951), boiling point 299°-300° C.).

8.0 g of 1,3-di(n-butoxy)benzene are transformed into 2,6-di(n-butoxy)benzaldehyde operating in a way similar to that disclosed for the preparation of 2,6-diethoxybenzaldehyde (example 1), said 2,6-di(n-butoxy)benzaldehyde being distilled at 134°-137° C./0.08 Torr and being further purified by crystallization from n-pentane at −70° C.; yield is of 47%. I.R. (film) 1684 cm$^{-1}$ (C=O), 1593 cm$^{-1}$ (phenyl), 1250 cm$^{-1}$ (aromatic C—O), 777 cm$^{-1}$ (phenyl).

2.58 g of 2,6-di(n-butoxy)benzaldehyde in 25 ml of 95% ethanol are added with 2.60 g of hydroxylamine hydrochloride and 25 ml of pyridine. Said mixture is refluxed for one hour and then it is poured into 200 ml of water at 0° C. so that an oil is separated that immediately becomes a solid. Said solid after filtering and crystallization from benzene/n-hexane gives the oxime of 2,6-di(n-butoxy)benzaldehyde with yield of 82%; melting point is 90°-91° C.

2.10 g of the oxime of 2,6-di(n-butoxy)benzaldehyde are transformed into 2,6-di(n-butoxy)benzylamine hydrochloride operating in a way similar to that disclosed for the preparation of 2,6-diethoxybenzylamine hydrochloride (example 1) with the exception that the treatment with gaseous hydrogen chloride is carried out in a n-pentane solution instead of using an ethyl ether solution; 2,6-di(n-butoxy)-benzylamine hydrochloride so obtained shows after crystallization from ethanol/ethyl ether mixture at −30° C. a melting point of 147°-149° C.; yield is 79%. I.R. (KBr) 2600 cm$^{-1}$ (NH$_3$+), 1253 cm$^{-1}$ (aromatic C—O), 773 cm$^{-1}$ (phenyl).

Activity of the compound as an inhibitor and as a substrate

BAO: n=4, $IC_{50}(M) = 1.40 \pm 0.01 \times 10^{-7}$, pr, nc, ns;

DAO: $IC_{50}(M) > 1 \times 10^{-3}$, s;

LAO: $IC_{50}(M) > 1 \times 10^{-3}$;

MAO: $IC_{50}(M) > 1 \times 10^{-3}$, ns.

EXAMPLE 5

Synthesis and activity of an inhibitor of the formula:

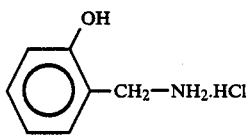

2.0 g of salicylaldoxime are reduced to 2-hydroxybenzylamine following the procedure disclosed by R. C. Raiford, E. P. Clark (J. Am. Chem. Soc., 45, 1738 (1923)), said 2-hydroxybenzylamine showing a melting point of 128°-129° C. (value found in the literature 126°-129° C.) after crystallization from an ethyl ether/n-pentane mixture at −30° C. followed by sublimation at 100° C./0.1 Torr.

A solution of 1.50 g of 2-hydroxybenzylamine in 400 ml of anhydrous ethyl ether is saturated with gaseous hydrogen chloride so that 2-hydroxybenzylamine hydrochloride is formed which is dried under reduced pressure and recrystallized from acetonitrile so as to show a melting point of 150° C.; yield is 95%. I.R. (KBr) 3285 cm$^{-1}$ (OH), 2585 cm$^{-1}$ (NH$_3$+), 1240 cm$^{-1}$ (C—O), 757 cm$^{-1}$ (phenyl).

Activity of the compound as an inhibitor and as a substrate

BAO: n=2, $IC_{50}(M) = 1 \times 10^{-3}$, s;

DAO: n=2, $IC_{50}(M) = 1 \times 10^{-3}$, s;

LAO: $IC_{50}(M) > 1 \times 10^{-3}$;

MAO: $IC_{50}(M) > 1 \times 10^{-3}$, ns.

EXAMPLE 6

Preparation and activity of the inhibitor of the formula:

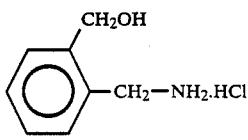

4.92 g of phthalide are transformed according to C. Y. Belke, S. C. K. Su, J. A. Shafer (J. Am. Chem. Soc., 93, 4552 (1971)), into 2-hydroxymethylbenzamide (melting point 147°–149° C.) which by treatment with lithium-aluminium hydride according to R. M. Laird, R. E. Parker (J. Chem. Soc., 4784 (1965)), and then with gaseous hydrogen chloride dissolved in ethyl ether, gives 2-hydroxymethylbenzylamine hydrochloride which after crystallization from an ethanol/ethyl ether mixture shows melting point of 177°–179° C. (G. Pifferi, L. Fontanella, E. Decelli, R. Monguzzi, J. Heterocyclic Chem., 9, 1209 (1972), melting point 177°–178° C.). I.R. (KBr) 3260 cm$^{-1}$ (OH), 2595 cm$^{-1}$ (NH$_3$+), 1020 cm$^{-1}$ (C—O), 760 cm$^{-1}$ (phenyl).

Activity of the compound as an inhibitor and as a substrate

BAO: n=2, $IC_{50}(M) = 1 \times 10^{-3}$, s;

DAO: n=2, $IC_{50}(M) > 1 \times 10^{-3}$, s;

LAO: $IC_{50}(M) > 1 \times 10^{-3}$;

MAO: $IC_{50}(M) > 1 \times 10^{-3}$, ns.

EXAMPLE 7

Synthesis and activity of the inhibitor of the formula

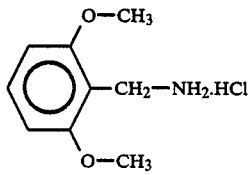

5.0 of 2,6-dimethoxybenzoic acid suspended in 200 ml of anhydrous methylene chloride are added with 7.65 ml of triethylamine and then with 3.6 ml of oxalyl chloride. The mixture after being stirred at room temperature for three hours is concentrated under reduced pressure, cooled with ice, added with 10 ml of concentrated ammonia, then stirred for half an hour, then again evaporated under reduced pressure, taken with water and filtered. The solid so obtained, after crystallization from methanol, gives 2,6-dimethoxybenzamide with melting point 208°–209° C.; yield is 54%.

2.0 g of 2,6-dimethoxybenzamide dissolved in 200 ml of anhydrous tetrahydrofuran are added over a period of 15 minutes to a suspension of 1.0 g of lithium-aluminium hydride in 20 ml of tetrahydrofuran. The mixture is refluxed for 8 hours, then it is added with caution with water till the evolution of gas ends, then with 15% sodium hydroxide, and filtered in order to remove the solid matter. The solution so obtained gives, after drying with solid potassium hydroxide followed by elimination of the solvent under reduced pressure and crystallization from n-hexane, 2,6-dimethoxybenzylamine with melting point 83°–85° C.; the yield is 82%. Said amine, after treatment with gaseous hydrogen chloride in anhydrous ethyl ether and crystallization of the product from acetonitrile, gives with 94% yield the 2,6-di-methoxybenzylamine hydrochloride having melting point of 228°–230° C. (E. Bach, A. Kjaer, Acta Chem. Scand., 25, 2629 (1971), 225°–226° C. from ether). I.R. (KBr) 2620 cm$^{-1}$ (NH$_3$+), 1263 cm$^{-1}$ (aromatic C—O), 780 cm$^{-1}$ (phenyl).

Activity of the compound as an inhibitor and as a substrate

BAO: n=4, $IC_{50}(M) = 1.2 \pm 0.2 \times 10^{-4}$, r, m, ns;

DAO: n=4, $IC_{50}(M) = 5.6 \pm 0.3 \times 10^{-3}$, s;

LAO: $IC_{50}(M) > 1 \times 10^{-3}$;

MAO: n=4, $IC_{50}(M) = 1.9 \pm 0.2 \times 10^{-4}$, s weak

EXAMPLE 8

Synthesis and activity of the inhibitor of the formula

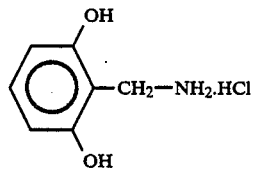

1.60 g of 2,6-dimethoxybenzylamine are dissolved into 10 ml of 48% water solution of hydrogen bromide and refluxed for 3 hours. The mixture is evaporated under reduced pressure, then added with 10 ml of concentrated hydrochloric acid and evaporated again. The treatment with hydrochloric acid is repeated twice till disappearance of the bromide ion so as to obtain 2,6-dihydroxybenzylamine hydrochloride which, after crystallization from an ethanol/ethyl ether mixture, shows a melting point of 203°–205° C. (with decomposition); the yield is 95%. I.R. (KBr) 3280 cm$^{-1}$ (OH), 2580 cm$^{-1}$ (NH$_3$+), 785 cm$^{-1}$ (phenyl).

Activity of the compound as an inhibitor and as a substrate

BAO: n=2, $IC_{50}(M) = 1 \times 10^{-3}$;

DAO: $IC_{50}(M) > 1 \times 10^{-3}$;

LAO: $IC_{50}(M) > 1 \times 10^{-3}$;

MAO: $IC_{50}(M) > 1 \times 10^{-3}$.

EXAMPLE 9

Synthesis and activity of the inhibitor of the formula

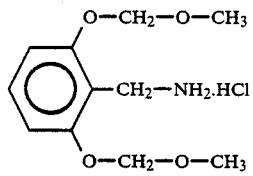

3 g of 2,6-bis(methoxymethoxy)benzaldehyde prepared according to C. A. Townsend, S. G. Davis, S. G. Christensen, J. C. Link, O. P. Lewis, J. Am. Chem. Soc., 103, 6885 (1981), added with a solution of 0.936 g of NaOH in 4 ml of water, are treated with 1.10 g of hydroxylamine hydrochloride. The mixture is stirred till it is converted into a semisolid matter, then it is added with 20 ml of water and saturated with $CO_2$. The solid so precipitated is filtered, then washed with water and dried under vacuum so as to obtain the oxime of the 2,6-bis(methoxymethoxy)benzaldehyde with melting point of 133°-134° C.; the yield is 96%.

3.06 g of the oxime of 2,6-bis(methoxymethoxy)benzaldehyde in 39 ml of 95% ethanol and 39 ml of 2N NaOH are treated with 2.86 g of the nickel/aluminium Raney Alloy. After stirring the mixture for 30 minutes at room temperature, nickel is removed by filtration and it is washed with ethanol. The solution is cooled to 0° C., then acidified with 0.5 N HCl at 0° C., washed just once with dichloromethane, then adjusted to pH=12 with a 20% solution of potassium hydroxide and extracted with 100 ml of ethyl ether, such volume being divided into three portions. The extract are dried with solid KOH and, after elimination of the solvent, they give 2,6-bis(methoxymethoxy)benzylamine which distils off at 125° C./0.05 Torr; the yield obtained is 70%.

1.09 g of 2,6-bis(methoxymethoxy)benzylamine in 60 ml of anhydrous ethyl ether are treated with 1.92 ml of a 2.25 M solution of hydrogen chloride in anhydrous ethyl ether. A white solid precipitates which after filtering and carefully washing with anhydrous ethyl ether gives 2,6-bis(methoxymethoxy)benzylamine hydrochloride with melting point 151,5°-152° C.; the yield obtained is 95%. I.R. (KBr) 2580 cm$^{-1}$ ($NH_3^+$), 1252 cm$^{-1}$ (aromatic C—O), 1076 cm$^{-1}$ (acetalic C—O), 773 cm$^{-1}$ (phenyl).

Activity of the compound as an inhibitor and as a substrate

BAO: n=4, $IC_{50}(M)=9.5\pm0.7\times10^{-7}$, r, m, s;

DAO: $IC_{50}(M)>1\times10^{-2}$, s;

LAO: $IC_{50}(M)>1\times10^{-3}$;

MAO: n=4, $IC_{50}(M)=2.2\pm0.6\times10^{-2}$, ns.

EXAMPLE 10

Synthesis and activity of the inhibitor of the formula

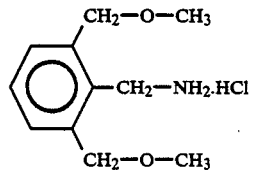

2.0 g of 2,6-bis(bromomethyl)benzonitrile (F. Voegtle, P. Neumann, M. Zuber, Chem. Ber., 105, 2955 (1972)), prepared starting from 2,6-dimethylaniline by the Sandmayer reaction with cupreous cyanide and next by the bromination with N-bromosuccinimide, are dissolved in 2 ml of anhydrous N,N-dimethylformamide and added to the suspension of 1.24 g of sodium methylate in 10 ml of N,N-dimethylformamide at 0° C. After stirring the mixture for three hours at 0° C., the same is added with 20 ml of water and extracted with 120 ml of ethyl ether divided into three portions. The extracts, after drying with anhydrous sodium sulfate and evaporation to dryness, give a solid residue which, after sublimation at 100° C./0.04 Torr, gives 2,6-bis(methoxymethyl)benzonitrile with melting point 80°-81° C.; the yield obtained is 40%.

0.86 g of 2,6-bis(methoxymethyl)benzonitrile, dissolved into 100 ml of anhydrous ehtyl ether, added over a period of 10 minutes to a suspension of 0.34 g of lithium-aluminium hydride in 50 ml of anhydrous ethyl ether. The mixture is refluxed for 6 hours, then it is hydrolyzed with 6 ml of a 10% solution of sodium hydroxide and filtered washing the filter with ethyl ether. The ethereal solution after drying with solid KOH and evaporation down to a volume of about 50 ml, is saturated with gaseous hydrogen chloride. The solid is filtered, washed with ethyl ether, dried under vacuum and crystallized from acetonitrile, so as to give the 2,6-bis(methoxymethyl)benzylamine hydrochloride with melting point 167°-168° C.; the yield obtained is 88%. I.R. (KBr) 1075 cm$^{-1}$ (the ether group), 795 cm$^{-1}$ (phenyl).

Activity of the compound as an inhibitor and as a substrate

BAO: n=4, $IC_{50}(M)=1\pm0.45\times10E-3$, pr, m, ns;

DAO: $IC_{50}(M)>1\times10^{-3}$, s;

LAO: $IC_{50}(M)>1\times10^{-3}$;

MAO: n=2, $IC_{50}(M)>1\times10^{-3}$, ns.

EXAMPLE 11

Synthesis and activity of the inhibitor of the formula

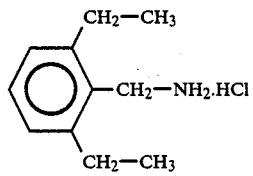

1.59 g of 2,6-diethylbenzonitrile, prepared according to the procedure of D. J. Foster, D. E. Reed Jr. (J. Org. Chem. 26, 252 (1961)) starting from 2,6-diethylaniline by the Sandmayer reaction with cupreous cyanide, are dissolved into 50 ml of anhydrous ethyl ether and rapidly added to a suspension of 0.90 g lithium-aluminium hydride in 60 ml of ethyl ether. After refluxing the mixture for 6 hours, it is hydrolyzed with 6 ml of a 10% water solution of sodium hydroxide and extracted with ethyl ether, then the extracts collected are filtered. The ethereal solution after filtering and drying with solid potassium hydroxide and total removal of the solvent under reduced pressure, is extracted with 50 ml of anhydrous ethyl ether and saturated with gaseous hydrogen chloride. A precipitate is formed which after filtering, washing with anhydrous ethyl ether, drying under vacuum and crystallization from acetonitrile, gives the 2,6-diethylbenzylamine hydrochloride with melting point of 243°-245° C.; the yield obtained is 77% I.R. (KBr) 2600 cm$^{-1}$ ($NH_3^+$), 761 cm$^{-1}$ (phenyl).

Activity of the compound as an inhibitor and a substrate

BAO: n=4, $IC_{50}(M)=4.3\pm0.4\times10^{-4}$, r, nc, ns;

DAO: $IC_{50}(M)>1\times10^{-3}$, s;

LAO: $IC_{50}(M)>1\times10^{-3}$;

MAO: $IC_{50}(M)>1\times10^{-3}$, s.

EXAMPLE 12

Synthesis and activity of the inhibitor of the formula

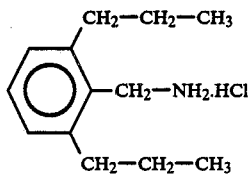

14.34 g of the 2,6-difluorobenzoic acid chloride and 14.52 g of 2-amino-2-methyl-1-propanol are transformed in a way similar to the procedure according to A. I. Meyers, D. L. Temple, D. Haidukewich, E. D. Mihelich (J. Org. Chem. 39, 2787 (1974)) into N-(2-hydroxy-1,1-di-methylethyl)-2,6-difluorobenzamide (melting point 110°-112° C.) and next they are cyclized in the presence of thionyl chloride to 2-(2,6-difluorophenyl)-4,5-dihydro-4,4-dimethyl-1,3-oxazole. The latter compound is transformed by extending the procedure according to A. I. Meyers and B. E. Williams (Tetrahedron Lett. (1978), 223), with n-propylmagnesium bromide into 2-(2,6-dipropylphenyl)-4,5-dihydro-4,4-dimethyl-1,3-oxazole that, according to the procedure of A. I. Meyers, R. J. Himmelsbach, M. Reuman (J. Org. Chem. 48, 4053 (1983)), is reduced with lithium and liquid ammonia to a 2-[[(2,6-dipropylphenyl)methyl]-amino]-2-methyl-1-propanol and then oxidized to 2,6-dipropylbenzaldehyde by treatment with N-chlorosuccinimide, with dehydrohalogenation carried out employing basic alumina followed by hydrolysis. 2.50 g of 2,6-dipropylbenzaldehyde in 20 ml of pyridine are added with 2.74 g of hydroxylamine hydrochloride, then heated for one hour on a water bath, treated with 40 ml of water, adjusted to pH=1 with concentrated hydrochloric acid and then extracted with 250 ml of ethyl ether, said volume being divided into five portions. The extracts give after drying with anhydrous sodium sulfate and evaporation of the solvent under reduced pressure the oxime compound in the form of a raw oil with a yield of 92%. 2.16 g of the oxime are dissolved into 24 ml of anhydrous tetrahydrofuran and added with stirring and under a blanket of nitrogen to a solution of 21.12 mmoles of AlH₃ in 28.8 ml of tetrahydrofuran prepared according to N. M. Yoon, H. C. Braun (J. Am. Chem. Soc., 90, 2927 (1968)). After refluxing the mixture for one hour, it is hydrolyzed with 2 ml of water to which 2 ml of 10% NaOH are added, then the mixture is filtered and the solid is carefully washed with 150 ml of ethyl ether. The ethereal solution is added to the filtered tetrahydrofuran phase and the whole is dried with solid potassium hydroxide. An oil is obtained as a residue after removal of the solvent under reduced pressure, said oil being then diluted with 40 ml of anhydrous ethyl ether, then saturated with gaseous hydrogen chloride, filtered, washed with anhydrous ethyl ether and dried under vacuum. 2,6-di-n-propylbenzylamine hydrochloride is obtained with melting point 220°-222° C. by crystallization from acetonitrile; the yield is 70%. I.R. (KBr) 2610 cm⁻¹ ($NH_3^+$), 764 cm⁻¹ (phenyl).

Activity of the compound as an inhibitor and as a substrate

BAO: n=4, $IC_{50}(M)=1.5\pm0.2\times10^{-5}$, r, nc, ns;

DAO: $IC_{50}(M)$ $1\times10^{-3}$, s weak;

LAO: $IC_{50}(M)$ $1\times10^{-3}$;

MAO: $IC_{50}(M)$ $1\times10^{-3}$, s.

EXAMPLE 13

Synthesis and activity of the inhibitor of the formula

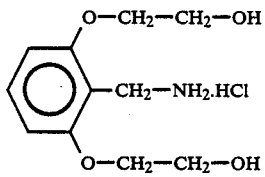

10 g of resorcinol reacted in a way similar to that disclosed for the preparation of 1,3-diethoxybenzene (example 1), with a solution in N,N-dimethylformamide of 2-(2-bromoethoxy)tetrahydropyran prepared according to the procedure of D. T. Witiak, G. K. Poochikian, D. R. Feller, N. A. Kenfield, H. A. I. Newmann (J. Med. Chem., 18, 992 (1975); C.A. 83, 201848v (1975)), are transformed into bistetrahydropyranyl derivative of 1,3-bis(2-hydroxyethoxy)benzene with a yield of 85%, said derivative so obtained being recovered from the reaction mixture by extraction with ethyl ether instead of employing benzene and then dried with solid potassium hydroxide. I. R. (film) 1262 cm⁻¹ (aromatic C-O), 1073 cm⁻¹ (acetalic C-O)8 762 cm⁻¹ (phenyl).

20.19 g of the bistetrahydropyranyl derivative of the 1,3-bis-(2-hydroxyethoxy)benzene are transformed into the bistetrahydropyranyl derivative of the 2,6-bis(2-hydroxyethoxy)benzaldehyde with a yield of 46%, by a procedure similar to that disclosed for the preparation of 2,6-diethoxybenzaldehyde (example 1) with the exception that when the hydrolysis is performed no hydrochloric acid is added and that the purification of the product is carried out by flash chromatography on Merck silica gel 60 (230–400 mesh and eluting with a mixture of petroleum ether (boiling point 40°-60° C.)/ethyl acetate (4/6). I.R. of the product (film): 1684 cm⁻¹ (C=O), 1255 cm⁻¹ (aromatic C—O), 1075 cm⁻¹ (acetalic C—O), 778 cm⁻¹ (phenyl).

24.33 g of the bistetrahydropyranyl derivative of the 2,6-bis-(2-hydroxyethoxy)benzaldehyde in 80 ml of methanol are stirred at room temperature for 4 hours with 30 ml of water and 8 ml of concentrated hydrochloric acid, and then extracted with ethyl acetate. The organic extracts give after drying with anhydrous sodium sulfate and elimination of the solvent under reduced pressure, the 2,6-bis-(2-hydroxyethoxy)benzaldehyde which is then purified by crystallization from ethyl acetate; the yield is 57%; melting point is 101°–103° C. I.R. (KBr) 3410 cm$^{-1}$ (OH), 1672 cm$^{-1}$ (C=O), 1255 cm$^{-1}$ (aromatic C—O), 775 cm$^{-1}$ (phenyl).

5.08 g of 2,6-bis(2-hydroxyethoxy)benzaldehyde dissolved in 100 ml of anhydrous methanol are treated with 15.6 g of ammonium acetate and 12 g of sodium cyanoborohydride, then stirred under nitrogen blanket at 25°–30° C. for 48 hours, then adjusted to pH=1 with concentrated hydrochloric acid and evaporated at reduced pressure. The solid residue is treated with 30 ml of water and extracted with 20 ml of ethyl acetate, said volume being divided previously into two portions. The water phase, after elimination of the small amount of ethyl acetate dissolved, such removal being carried out under reduced pressure, is adjusted to pH=11 with a 25% solution of potassium hydroxide and then extracted with tetrahydrofuran. The extracts are dried with anhydrous potassium carbonate, then evaporated under reduced pressure, dissolved with 30 ml of a 1/1 mixture of tetrahydrofuran/ethyl ether, and afterwards saturated with gaseous hydrogen chloride and filtered. The solid, after washing with anhydrous ethyl ether, drying under reduced pressure and crystallization from a mixture of ethanol/acetonitrile, gives 2,6-bis(hydroxyethoxy)benzylamine hydrochloride with a yield of 92%; melting point is 166°–168° C. I.R. (KBr), 3325 cm$^{-1}$ (OH), 2605 cm$^{-1}$ (NH$_3$+), 1262 cm$^{-1}$ (aromatic C—O), 779 cm$^{-1}$ (phenyl).

Activity of the compound as an inhibitor and as a substrate

BAO: n=4, $IC_{50}(M)=2.6\pm0.2\times10^{-6}$, pr, m, ns;

DAO: $IC_{50}(M)>1\times10^{-3}$, s;

LAO: $IC_{50}(M)>1\times10^{-3}$;

MAO: $IC_{50}(M)>1\times10^{-3}$, ns.

The present invention has been disclosed for illustrative and not for limitative purposes by illustrating some of its preferred embodiments, but it is to be understood that modifications and changes can be introduced in the same by those skilled in the art without departing from the spirit and scope of the invention for which a priority right is claimed.

What is claimed is:

1. A process for inhibiting the catalytic activity of at least one benzylaminoxidase in a material containing said benzylaminoxidase comprising contacting said material with a catalytic-inhibiting effective amount of a compound having the general formula

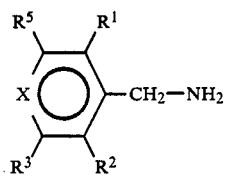

wherein

X is a C—R$^4$ group or a nitrogen atom;

R$^1$ and R$^2$, which can be the same or different from each other, represent a member selected from the group consisting of hydrogen, hydroxyl, alkoxyl, alkyl, alkenyl, hydroxyalkyl, hydroxyalkyoxyl phenoxyl, phenoxyalkyl, alkoxyalkyl, hydroxyalkoxyalkyl, alkoxyalkoxyl and hydroxyalkoxyalkoxyl groups, provided that no more than one of R$^1$ and R$^2$ is selected from the group consisting of hydrogen and hydroxyl, and R$^3$, R$^4$ and R$^5$, which can be the same or different form each other, represent a member selected from the group consisting of hydrogen, hydroxyl, halogens, alkyl, alkoxyl, hydroxyalkyl, hydroxyalkoxyl, haloalkyl, alkyl-carbonyl, ester, hydroxyalkoxyalkyl, carboxyl, amido, nitrile, sulfonic and nitro groups.

2. A process according to claim 1 wherein said X is a CH group or a nitrogen atom and R$^3$ and R$^5$ represent hydrogen.

3. A process according to claim 2 wherein the catalytic-inhibiting compound comprises 2,6-diethoxybenzylamine.

4. A process according to claim 2, wherein the catalytic-inhibiting compound comprises 2,6-di(n-propoxy)benzylamine.

5. A process according to claim 2, wherein the catalytic-inhibiting compound comprises 2,6-diisopropoxybenzylamine.

6. A process according to claim 2, wherein the catalytic-inhibiting compound comprises 2,6-di-(n-butoxy)benzylamine.

7. A process according to claim 2, wherein the catalytic-inhibiting compound comprises 2,6-bis(methoxymethoxy)benzylamine.

8. A process according to claim 2, wherein the catalytic-inhibiting compound comprises 2,6-bis(methoxymethyl)benzylamine.

9. A process according to claim 2, wherein the catalytic-inhibiting compound comprises 2,6-diethylbenzylamine.

10. A process according to claim 2, wherein the catalytic-inhibiting compound comprises 2,6-di-n-propylbenzylamine.

11. A process according to claim 2, wherein the catalytic-inhibiting compound comprises 2,6-bis(2-hydroxyethoxy)benzylamine.

* * * * *